US00PP14406P29

(12) United States Plant Patent
Harbaugh

(10) Patent No.: US PP14,406 P2
(45) Date of Patent: Dec. 23, 2003

(54) CALADIUM PLANT NAMED 'FLORIDA BLIZZARD'

(50) Latin Name: *Caladium×hortulanum*
Varietal Denomination: Florida Blizzard

(75) Inventor: Brent K. Harbaugh, Bradenton, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 10/291,042

(22) Filed: Nov. 8, 2002

(51) Int. Cl.[7] ..... A01H 5/00
(52) U.S. Cl. ..... Plt./373
(58) Field of Search ..... Plt./373

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Caladium plant named 'Florida Blizzard', characterized by its compact and densely-foliated plant habit suitable for container production; upright, outwardly spreading and symmetrical plant form; and white and dark green bi-colored leaves.

1 Drawing Sheet

Botanical classification/cultivar designation: *Caladium× hortulanum* cultivar Florida Blizzard.

BACKGROUND OF THE INVENTION

The present Invention relates to a new and distinct cultivar of Caladium plant, botanically known as *Caladium× hortulanum,* commercially referred to as a fancy-leaf Caladium, and hereinafter referred to by the cultivar name Florida Blizzard.

The new cultivar is a product of a planned and controlled breeding program conducted by the Inventor in Bradenton, Fla. The objective of the breeding program is to create densely-foliated compact Caladium cultivars with uniquely variegated foliage.

The new cultivar originated from a cross-pollination in 1992 of the *Caladium×hortulanum* cultivar Aaron, not patented, as the female, or seed, parent, with the *Caladium× hortulanum* cultivar White Christmas, not patented, as the male, or pollen, parent. The cultivar Florida Blizzard was discovered and selected in 1993 as a plant within the progeny of the stated cross-pollination in a controlled environment in Bradenton, Fla.

Asexual propagation of the new cultivar by tuber divisions in Bradenton, Fla., has shown that the unique features of this new Caladium plant are stable and reproduced true to type in successive generations of asexual propagation.

SUMMARY OF THE INVENTION

The new Caladium has not been observed under all possible environmental conditions. The phenotype may vary somewhat with variations in environment such as temperature and light intensity, without, however, any variance in genotype.

The following traits have been repeatedly observed and are determined to be the unique characteristics of 'Florida Blizzard'. These characteristics in combination distinguish 'Florida Blizzard' as a new and distinct cultivar:

1. Compact and densely-foliated plant habit suitable for container production.
2. Upright, outwardly spreading and symmetrical plant form.
3. White and dark green bi-colored leaves.

Plants of the new Caladium can be compared to plants of the female parent, the cultivar Aaron. When grown in side-side comparisons in Bradenton, Fla., plants of the new Caladium differed from plants of the cultivar Aaron, in the following characteristics:

1. Plants of the new Caladium had more leaves per plant than plants of the cultivar Aaron.
2. Plants of the new Caladium had white and dark green bi-colored leaves whereas plants of the cultivar Aaron had mostly white-colored leaves.

Plants of the new Caladium can be compared to plants of the male parent, the cultivar White Christmas. When grown in side-side comparisons in Bradenton, Fla., plants of the new Caladium differed from plants of the cultivar White Christmas, in the following characteristics:

1. Plants of the new Caladium were slightly taller than plants of the cultivar White Christmas.
2. Plants of the new Caladium had shorter leaves, but more leaves per plant than plants of the cultivar White Christmas.
3. Leaves of plants of the new Caladium had white-colored veins whereas leaves of plants of the cultivar White Christmas had green-colored veins.

Plants of the new Caladium can also be compared to plants of the cultivar Candidum, not patented. When grown in side-side comparisons in Bradenton, Fla., plants of the new Caladium differed from plants of the cultivar Candidum, in the following characteristics:

1. Plants of the new Caladium were slightly taller than plants of the cultivar Candidum.
2. Leaves of plants of the new Caladium had white-colored veins whereas leaves of plants of the cultivar Candidum had green-colored veins.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Caladium. The photograph is a side perspective view of a typical plant of 'Florida Blizzard' grown in a container.

DETAILED BOTANICAL DESCRIPTION

The aforementioned photograph, following observations, measurements and comparisons describe seven-week old plants (from planting a tuber division) grown in Bradenton, Fla. during the spring and summer in a shaded glass-covered greenhouse and under commercial production conditions in 15-cm containers. During the production of the plants, day temperatures were about 32° C., night temperatures were about 21° C. and light levels were about 2,000 to 3,000 foot-candies.

In the following description, color references are made to The Royal Horticultural Society Colour Chart except where general terms of ordinary dictionary significance are used.

Botanical classification: *Caladium×hortulanum* cultivar Florida Blizzard.

Parentage:

*Female, or seed, parent.*—*Caladium×hortulanum* cultivar Aaron, not patented.

*Male, or pollen, parent.*—*Caladium×hortulanum* cultivar White Christmas, not patented.

Propagation:

*Type.*—By tuber divisions.

*Tuber description.*—Number of dominant buds per tuber: About 7 to 9. Diameter: About 6.4 to 8.9 cm. Color: Epidermis, 200C; interior, 8B.

*Time to initiate roots on a tuber division.*—About 9 days at 27° C.

*Time to produce a fully rooted tuber division.*—About 37 days at 27° C.

*Root description.*—Dense, thick and white in color.

Plant description:

*Plant habit.*—Compact and densely-foliated, suitable for 10 to 20-cm containers.

*Plant form.*—Upright, outwardly spreading and symmetrical plant habit.

*Growth habit.*—Mostly erect when leaves are developing, becoming outwardly spreading as leaves develop.

*Plant height.*—About 44 cm from soil level to top of leaf plane.

*Plant spread.*—About 48 cm.

*Foliage description.*—Quantity: About 34 per plant. Length: About 21 cm. Width: About 15 cm. Shape: Cordate. Apex: Acute. Base: Cordate to somewhat sagittate. Margin: Entire. Aspect: Initially upright, then outwardly spreading. Texture, upper and lower surfaces: Smooth, glabrous, durable and flexible. Venation pattern: Penniform. Color: Upper surface: Interveinal areas, 137A; overlain with irregular, large and white, close to 155C, blotches; margin, 137A; venation, close to 155C; spot at petiole attachment and 1 mm wide line to leaf base, close to 185A. Lower surface: Margins and primary veins, 191A; irregular interveinal blotches and secondary veins, white, close to 155C. Petiole: Aspect: Mostly erect. Length: About 44 cm. Diameter: About 3 to 6 mm. Strength: Strong. Color: 147A.

*Flower description.*—Flower development has not been observed on plants of the new Caladium.

Disease/pest resistance: Plants of the new Caladium have not been observed to be resistant to pathogens or pests common to Caladium.

Temperature/weather tolerance: Plants of the new Caladium have been observed to be tolerant to temperatures as low as 10° C. and as high as 38° C. Plants of the new Caladium have been observed to be tolerant to rain and wind.

It is claimed:

1. A new and distinct cultivar of Caladium plant named 'Florida Blizzard', as illustrated and described.

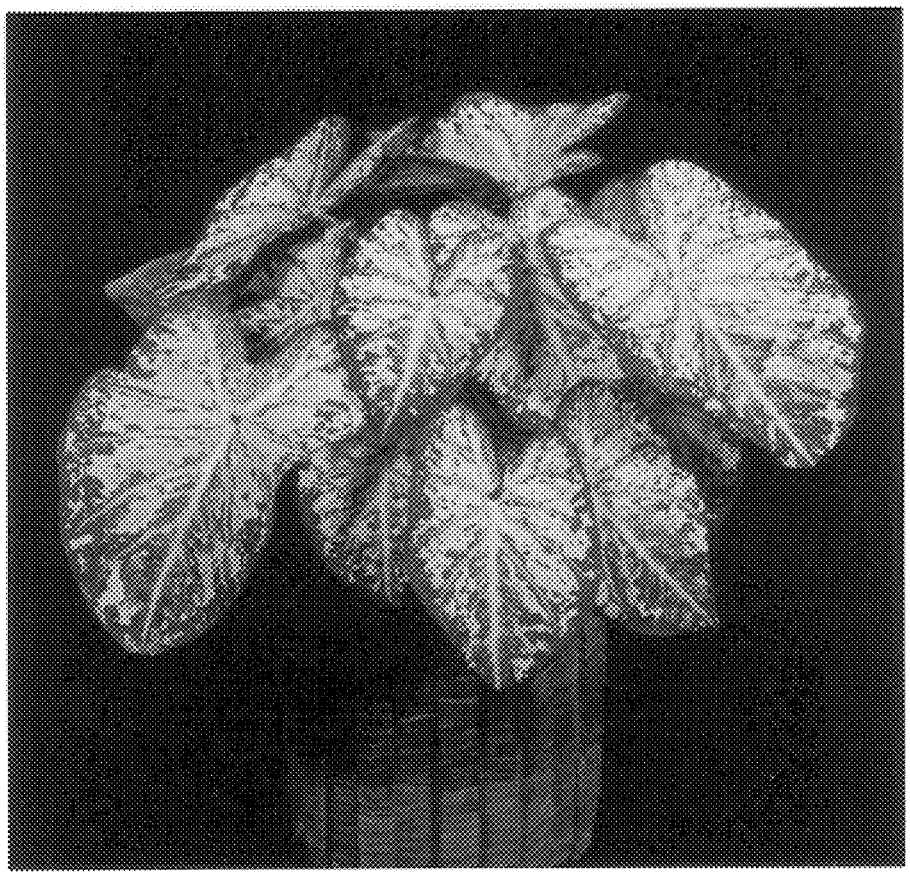

* * * * *